United States Patent [19]

Schenkel

[11] 4,394,388

[45] Jul. 19, 1983

[54] METHOD FOR THE CONTROL OF CATTLE GRUBS EMPLOYING M-PHENOXYBENZYL AND αCYANO-M-PHENOXYBENZYL ESTERS OF 2-HALOALKYL(OXY-, THIO-, SULFINYL-, OR SULFONYL)PHENYL ALKANOIC ACIDS

[75] Inventor: Robert H. Schenkel, Yardley, Pa.

[73] Assignee: American Cyanamid Company, Stamford, Conn.

[21] Appl. No.: 295,055

[22] Filed: Aug. 21, 1981

[51] Int. Cl.³ .................. A61K 31/275; A61K 31/235
[52] U.S. Cl. ..................................... 424/304; 424/308
[58] Field of Search ....................... 424/308, 309, 304

[56] References Cited

U.S. PATENT DOCUMENTS 4,199,595  4/1980  Berkelhammer et al. .......... 424/308

*Primary Examiner*—Sam Rosen
*Attorney, Agent, or Firm*—American Cyanamid Co.

[57] ABSTRACT

A method for the control of larvae of heel flies which parasitize ruminants and other domestic and farm animals involving topical application of a larvicidally effective amount of a m-phenoxybenzyl or α-cyano-m-phenoxybenzyl ester of a 2-haloalkyl(oxy-, thio-, sulfinyl-, or sulfonyl)phenyl alkanoic acid.

8 Claims, No Drawings

METHOD FOR THE CONTROL OF CATTLE GRUBS EMPLOYING M-PHENOXYBENZYL AND αCYANO-M-PHENOXYBENZYL ESTERS OF 2-HALOALKYL(OXY-, THIO-, SULFINYL-, OR SULFONYL)PHENYL ALKANOIC ACIDS

The invention herein described relates to a method for the control of larvae of the family Hypodermatidae. These parasites are also referred to as cattle grubs or ox warbles. They primarily infect ruminants such as cattle, goats and sheep, and on occasion attack other domestic and farm animals or even humans. Susceptible host animals can be protected from the ravages of cattle grubs by topical application of a larvicidally effective amount of m-phenoxybenzyl or α-cyano-m-phenoxybenzyl ester of a 2-haloalkyl(oxy-, thio-, sulfinyl-, or sulfonyl)phenyl alkanoic acid.

By way of background, these chemicals are disclosed in U.S. Pat. No. 4,199,595. This patent reveals that the above-mentioned esters are insecticidal and ixodicidal agents which are effective in controlling a variety of insects that attack important agricultural plants. However, this patent does not suggest that the compounds which are the subject of this invention are effective for controlling animal parasites which invade their hosts and damage or destroy flesh and/or hide.

Cattle grubs (or ox warbles) are the larvae of flies of the family Hypodermatidae, Genus Hypoderma (the heel flies). The best known species of this genus are: *Hypoderma lineatum,* the common cattle grub, and *Hypoderma bovis,* the northern cattle grub; the former is widely distributed on the North American Continent, Europe and Asia, while the latter is less commonly distributed.

If host animals are in a standing position, heel fly parasites generally attach their eggs to hairs on host's legs in the area from hock to the knee. However, when the host animal is bedded down, the eggs may be attached to hairs on other parts of the animal's body which come in contact with the ground. The eggs usually hatch within a week, and the resulting fly larvae bore directly into the skin or hair follicles of their hosts. The larvae then work upward between the muscles, and in several months find their way into the abdominal and chest cavities of the host. During the subsequent seven or eight months they continuously migrate over the surface of the paunch, intestines, spleen and other organs. They appear to have a special affinity for the muscular and mucous layers of the esophagus and gullet, as they are generally found there in the greatest numbers when compared to other internal locations. In the fall, winter, and spring the grubs migrate through the muscular tissues of the back and reach a location under the surface of the skin. Final development of the grubs takes place under the hide on the animal's back, where the now rapidly developing grubs can be found in swellings which have breathing holes produced by the grubs. Fully developed larvae eventually emerge from the skin, drop to the ground and crawl into loose soil where they pupate and finally emerge as warble flies, thus completing their life cycle.

Two general forms of physical injury are caused to animal hosts by parasitic larvae of the heel flies: (1) considerable irritation results from the migration of larvae through their host's tissues and subsequent emergence from the host's back; and (2) emergence of larvae from the host's back produces open wounds which attract tormenting insects (i.e., screw-worm flies).

In the United States alone, annual economic losses resulting from cattle grub infestations are estimated to be in the vicinity of one hundred million dollars. These losses are attributed to diminution of milk production in dairy animals, weight loss and depreciation of flesh value in meat animals, destruction of hides, and even deaths caused by the aberrant wild behavior of animals in their efforts to escape from flies and the irritation caused by the parasitic larvae of cattle grubs.

Cattle grubs present a danger to people engaged in the care and handling of ruminants or other susceptible domestic and farm animals which serve as hosts for this parasite. Such individuals are frequently exposed to cattle grubs and may occasionally be infected. Humans contracting this disease may suffer long-term debilitating effects, or in some cases even death, as a result of the attack of these parasites.

In light of the foregoing discussions of economic effects in the area of animal husbandry and also human health considerations, control of cattle grubs is highly desirable. An object of this invention is to provide a new and useful chemical method for the control of this noxious parasite. This object is manifest in the following description and particularly delineated in the appended claims.

It has been unexpectedly discovered that compounds of formula I, below, are highly effective grubicides useful in the control of heel fly larvae. The compounds which are utilized in this invention are the m-phenoxybenzyl and α-cyano-m-phenoxybenzyl esters of 2-haloalkyl (oxy-, thio-, sulfinyl-, or sulfonyl)phenyl alkanoic acids represented by the structural formula:

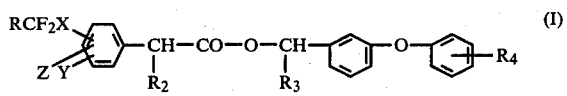

wherein $RCF_2X-$, Y and Z is each meta or para to the carbon to to which the alkanoic acid ester group is attached, and X is O, S, SO or $SO_2$; Y and Z is each H, Cl, F, Br, $NO_2$, $CH_3$ or $OCH_3$; R is H, F, $CHF_2$ or $CF_3$; $R_2$ is ethyl, n-propyl, isopropyl, isopropenyl or t-butyl; $R_3$ is H, CN or $-C\equiv CH$; and $R_4$ is H, F, Cl, $CH_3$ or $OCH_3$ or the optical isomers thereof.

Preferred compounds which are useful as grubicides effective for the control of Hypodermatidae larvae may be represented by the structural formula:

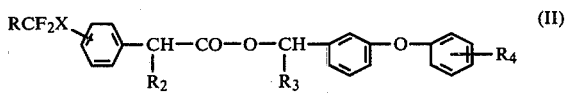

wherein $RCF_2X-$ is meta or para to the carbon to which the alkanoic acid ester group is attached; R is H or F; X is O or S; $R_2$ is ethyl, n-propyl or isopropyl; $R_3$ is H, or CN; and $R_4$ is H, F, Cl, $CH_3$ or $OCH_3$; and most preferred are those compounds where X is oxygen; R is H; $R_2$ is isopropyl; $R_3$ is cyano and $R_4$ is hydrogen and the optical isomers thereof, especially the compounds of this structure where the optical isomer is a $(+)$-acid and a $(\pm)$-alcohol.

It has been discovered that formula-I compounds, when applied topically to ruminants (i.e., cattle, sheep, goats) and other warm-blooded animals as a dilute solution, suspension, dispersion, dust, or dust concentrate, will control the larvae of heel flies. In order to effect control of cattle grubs with topically-applied formula-I preparations, animals should receive about 0.05 to 150 mg of formula-I compound per kg of animal body weight.

The compounds useful in the invention, as represented by formula I, may be conveniently formulated as dusts, dust concentrates, wettable powders, emulsifiable concentrates, and applied to host animals by conventional methods (i.e., spraying, dusting, dipping, etc.).

Wettable powders are prepared by grinding together a formula-I compound with an inert solid diluent to achieve a concentration of about 16 to 85% by weight of compound, and blending therewith about 5 to 10% by weight of a surfactant. The wettable powder is then generally dispersed in water or other suitable diluent for application as a dilute spray onto the host animal or locus where control is desired or for use as a bath when dipping animal hosts.

Solid formulations (i.e., dusts) can be prepared by grinding and blending together an inert solid diluent such as attapulgite, kaolin, walnut shell flour, corncob flour, diatomaceous earth or the like, and the active ingredient when such ingredient is a solid. When the active ingredient is a liquid, it may be sprayed on the carrier and thoroughly mixed therewith, or it may be dissolved in a solvent such as acetone, lower molecular weight alcohols, toluene, xylene and the like, and sprayed as a dilute solution on the solid carrier. Dusts usually contain from about 1 to 15% by weight of active ingredient and may be applied at this concentration to host animals and their habitats.

The formula-I m-phenoxybenzyl and α-cyano-m-phenoxybenzyl esters of 2-haloalkyl(oxy-, thio-, sulfinyl or sulfonyl)phenyl alkanoic acids may also be prepared as emulsifiable concentrates by dissolving or dispersing about 10 to 75% by weight of the active compound in a suitable solvent carrier (i.e., a petroleum distillate having a minimum aromatic content of 85%) and admixing therewith about 10% by weight of an emulsifier (i.e., polyoxyethylene condensates and blends of same with alkyl aryl sulfonates). These concentrates are also generally dispersed in water or other suitable solvent for application by spraying or dipping of the animal host.

Application of various liquid formulations of the formula-I pyrethroids are generally made with solutions, suspensions or dispersions, containing about 0.005 to 1.0% by weight and preferably 0.005 to 0.5% by weight of said formula-I compound.

The larvidical activity of the compounds of the invention may be conveniently evaluated by a method accepted by the U.S. Agricultural Research Service, in which mice infected with Cuterebra spp. are treated topically with the compounds under evaluation.

The following non-limiting Examples further serve to illustrate the invention.

EXAMPLE 1

Preparation of α-Isopropyl-4-difluoromethoxyphenylacetyl chloride

A solution of α-isopropyl-4-difluoromethoxyphenylacetic acid (1.2 g) and thionyl chloride (0.6 ml) in benzene (5 ml) is refluxed for 4 hours. Evaporation of the solvent and excess thionyl chloride gives the acid chloride which is used as such for esterification in Example 2.

EXAMPLE 2

Preparation of α-Cyano-m-phenoxybenzyl α-isopropyl-4-difluoromethoxyphenylacetate A solution of α-isopropyl-4-difluoromethoxyphenylacetyl chloride (4.58 mmol) in ether (5 ml) is added to an ether (20 ml) solution of α-cyano-m-phenoxybenzyl alcohol (4.58 mmol) and pyridine (0.5 ml). The mixture is stirred overnight and filtered. The filtrate and the washings are evaporated and the residual oil is purified on 5×20 cm silica gel plates using 1:1 methylenechloride-hexane as eluent. The band in the silica gel plate is extracted with ether and evaporated to give the desired ester as an oil.

NMR (CDCl$_3$) δ0.88 (four doublets, J=6 Hz, 6H, CH$_3$, 2.30 [m, 1H, —CH—CH(CH$_3$)$_2$], 3.24 [d, J=10.1 Hz, 1H, —CH—CH(CH$_3$)$_2$], 6.33 (two singlets, 1H, —CHCN), 6.45 (t, J=74 Hz, 1H, CHF$_2$O—) 7.16 (m, 13H, ArH).

Analysis calculated for C$_{26}$H$_{23}$+$_2$NO$_4$: C, 69.17%; H, 5.13%; F, 8.42%; N, 3.10%. Found: C, 69.41%; H, 5.20%; F, 10.25%; N, 3.70%.

EXAMPLE 3

Preparation of α-Isopropyl-4-difluoromethoxyphenylacetic acid

Into an 80° C. magnetically-stirred mixture of 10.00 g (0.0515 mol) of α-isopropyl-4-hydroxyphenylacetic acid, 65 ml of dioxane, 19.08 g (0.464 mol) of sodium hydroxide, and 30 ml of water is bubbled 46 g (0.532 mol) of chlorodifluoromethane over a period of 4 hours. The reaction mixture is poured into 250 ml of ice water and the resulting mixture is washed with ether, acidified with concentrated hydrochloric acid to pH 3, and then extracted with 200 ml of ether. The ether solution is washed once with 100 ml of water, dried with sodium sulfate, filtered, and then evaporated to give a white paste. A mixture of hexane and methylene chloride is added and the resulting mixture is filtered to remove the solid which is the starting material. The filtrate is evaporated to give 5.41 g of a clear brown oil. It is estimated that the product thus obtained is at least 85% pure as determined by NMR. NMR (CDCl$_3$-d$_5$ pyridine), δ7.43 (d, J=8.2 Hz, 2H), δ7.08 (d, J=8.2 Hz, 2H), δ6.57 (t, J=74.3 Hz, 1H), δ3.63 (s. imp.), δ3.25 (d, J=10 Hz, 1H), δ2.37 (m, 1H, δ1.19 (d, J=6.5 Hz, 3H, δ0.78 (d, J=6.5 Hz, 3H), δ13.82 (s, 1H).

EXAMPLE 4

Resolution of α-Isopropyl-4-difluoromethoxyphenylacetic acid

A warm solution (60° C.) of α-phenethylamine (4.96 g) in aqueous ethanol (60% ethanol, 20 ml) is added to a warm solution (60° C.) of the racemic acid (20 g) in aqueous ethanol (60% ethanol, 50 ml) with magnetic stirring. As the solution is allowed to cool slowly to room temperature, the salt precipitates out as a white crystalline solid. The mixture is allowed to stand overnight and the solids are collected by filtration, washed with aqueous ethanol (10 ml) and dried (9.5 g): m.p. 184°–188° C. The resolved acid obtained from the above salt is found to have a rotation $[\alpha]_D^{R.T.} = +37.1°$ (CHCL$_3$, C=1.439 g/100 ml). Two additional crystallizations of the above salt from aqueous ethanol (60% ethanol) produces white needles, m.p. 185°–187° C., from which the resolved acid is obtained with $[\alpha]_D^{R.T} = +40.4°$ (CHCl$_3$, C=1.353 g/100 ml).

EXAMPLE 5

Preparation of
(±)-α-Cyano-m-phenoxybenzyl(+)-α-isopropyl 4-difluoromethoxyphenylacetate The resolved (+)-acid obtained in the above example is converted to the ester using the procedures of Examples 1 and 2. $N_D^{23} = 1.5432$; NMR (CDCl$_3$) δ6.8 to 7.5 (m, 13H, ArH), 6.43 (t, J=74 Hz, 1H, OCHF$_2$), 6.30 and 6.23 (2S, 1H, CH—CN), 3.27 (d, J=10 Hz, 1H, CH—CH(CH$_3$)$_2$).

EXAMPLE 6

In Vivo Procedure for Evaluating Larvicidal Activity of Compounds of the Invention Using the Parasite Cuterebra sp. and Mice as Host Animals White mice are artificially infested nasally, buccally, or ocularly with 5 newly-hatched larvae of Cuterebra sp. For dermal tests, 48 hours later a plastic collar is placed around the neck of each male mouse, and the portion of the body behind the collar is dipped in 200 ml of an emulsion of a test compound. A standard emulsifiable concentrate consists of 25 parts of test compound, 65 parts of xylene and 10 parts octylphenoxy polyethoxy ethanol of average molecular weight equal to 628 and having from 9 to 10 ethylene oxide units.

The skin of each mouse is examined carefully for encapsulated live larvae four days after treatment. Effectiveness of the treatments is determined by comparing numbers of larvae encapsulated in treated mice with numbers found in untreated control mice. Usually 3 mice/concentration are treated. if mice or the larvae are killed at the initial concentration of 1%, lower concentrations (0.6, 0.3, 0.2, 0.1%, etc.) are tested until there is no systemic activity or the mice survive.

Mortality data are subjected to log-prohibit analysis in order to determine dosages or concentrations that kill 50 or 90% of the larvae.

The data obtained are recorded in Table I below.

TABLE I

Evaluation of Larvicidal Efficacy of Compounds of the invention for control of Cuterebra sp. using mice as test animals

| Treatment | Dermal (mice) Dosage % | |
|---|---|---|
| | LC$_{50}$ | LC$_{90}$ |
| α-cyano-m-phenoxybenzyl α-isopropyl-4-difluoromethoxyphenylacetate | .0067 | .015 |
| (±)-α-cyano-m-phenoxybenzyl (+)-α-isopropyl-4-difluoromethoxy phenylacetate | .0030 | .0056 |

I claim:

1. A method for protecting ruminant, domestic, and farm animals from infestation by the larvae of flies of the family Hypodermatidae comprising, applying topically to larvae-infested animals a larvicidally effective amount of a compound having the structural formula:

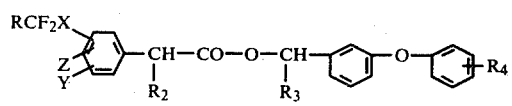

wherein RCF$_2$X—, Y and Z are all meta or para to the carbon to which the alkanoic acid ester group is attached, and X is O, S, SO or SO$_2$; Y and Z is each H, Cl, F, Br, NO$_2$, CH$_3$ or OCH$_3$; R is H, F, CHF$_2$ or CF$_3$; R$_2$ is ethyl, n-propyl, isopropyl, isopropenyl or t-butyl; R$_3$ is H, CN or —C≡CH; and R$_4$ is H, F, Cl, CH$_3$ or OCH$_3$ or the optical isomers thereof.

2. A method according to claim 1 wherein the compound has the formula:

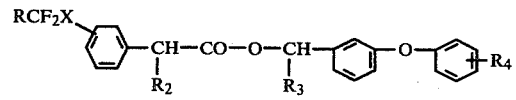

wherein RCF$_2$X— is meta or para to the carbon to which the alkanoic acid ester group is attached; R is H or F; X is O or S; R$_2$ is ethyl, n-propyl or isopropyl; R$_3$ is H or CN; and R$_4$ is H, F, Cl, CH$_3$ or OCH$_3$ and the optical isomers thereof, and the compound is applied to said animals' skin in an amount of from 0.05 to 150 mg/kg of animal body weight.

3. A method according to claim 2 wherein the compound is α-cyano-m-phenoxybenzyl α-isopropyl-4-difluoromethoxyphenylacetate.

4. A method according to claim 2 wherein the compound is (±) α-cyano-m-phenoxybenzyl (+) α-isopropyl-4-difluoromethoxyphenylacetate.

5. A method for protecting ruminant animals from infestation by the larvae of flies of the family Hypodermatidae comprising applying topically to the larvae-infested animals' skin a liquid solution containing from 0.005 to 1.0% by weight of a compound having the structural formula:

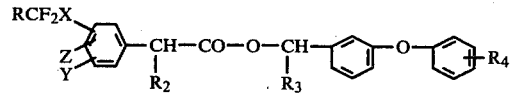

wherein RCF$_2$X—, Y and Z are all metal or para to the carbon to which the alkanoic acid ester group is attached, and X is O, S, SO or SO$_2$; Y and Z is each H, Cl, F, Br, NO$_2$, CH$_3$ or OCH$_3$; R is H, F, CHF$_2$ or CF$_3$; R$_2$ is ethyl, n-propyl, isopropyl, isopropenyl or t-butyl; R$_3$ is H, CN or —C≡CH; and R$_4$ is H, F, Cl, CH$_3$ or OCH$_3$ or the optical isomers thereof.

6. A method according to claim 5 wherein the compound has the structural formula:

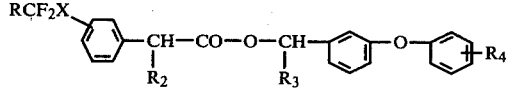

wherein RCF$_2$X— is meta or para to the carbon to which the alkanoic acid ester group is attached; R is H or F; X is O or S; R$_2$ is ethyl, n-propyl or isopropyl; R$_3$ is H or CN; and R$_4$ is H, F, Cl, CH$_3$ or OCH$_3$ or the optical isomers thereof.

7. A method according to claim 6 wherein said animals are cattle and said compound is α-cyano-m-phenoxybenzyl α-isopropyl-4-difluoromethoxyphenylacetate.

8. A method according to claim 6 wherein said animals are cattle and said compound is (+)-α-cyano-m-phenoxybenzyl (+)-α-isopropyl-4-difluoromethoxyphenylacetate.

* * * * *